United States Patent [19]

St. Georgiev et al.

[11] Patent Number: 4,719,306
[45] Date of Patent: Jan. 12, 1988

[54] SUBSTITUTED 3,5-DIPHENYL-3-(1H-IMIDAZOL-1-YLMETHYL)-2-METHYLISOXAZOLIDINES

[75] Inventors: Vassil St. Georgiev, Rochester; George B. Mullen, Avon, both of N.Y.

[73] Assignee: Pennwalt Corporation, Philadelphia, Pa.

[21] Appl. No.: 900,852

[22] Filed: Aug. 27, 1986

[51] Int. Cl.$^4$ .............................................. C07D 233/60
[52] U.S. Cl. ...................................... 548/240; 548/335
[58] Field of Search .......................................... 548/240

[56] References Cited

U.S. PATENT DOCUMENTS

| | | | |
|---|---|---|---|
| 3,711,495 | 1/1973 | Kulsa et al. | 548/240 |
| 3,915,978 | 10/1975 | Kulsa et al. | 548/240 |
| 3,987,179 | 10/1976 | Nadelson | 514/378 |

FOREIGN PATENT DOCUMENTS 54-76579  6/1979  Japan .

OTHER PUBLICATIONS

Sokolov, S. V. et al., Chemical Abstract 55:7399 (1961) Abstracting "Isoxazale Compounds III, Synthesis of Some Isoxazolylazoles", Zhur. Obshchei Khim. 30, pp. 1781–1787 (1960).
Kano, H. et al., Chem. Abstract 62:9139a (1965), Abstracting French 1,376,432 (Oct. 23, 1964).
Kano, H. et al., Chemical Abstract 63:8367a (1965), Abstracting French 1,380,177 (Nov. 27, 1964).
Takahi, Y. et al., Chemical Abstract 81:22233c (1974), Abstracting Japan Kokai 7399,336 (Dec. 15, 1973).
Boyce, C. B. et al., Chemical Abstract 87:23258a (1977), Abstracting German Offen. 2,639,189 (Mar. 10, 1977).
Funaki, Y. et al., Chemical Abstract 92:128915u (1980), Abstracting Japan Kokai 79 76,579 (Jun. 19, 1979).
Kelly, R. C. et al., Chemical Abstract 93:114498u (1980), Abstracting German Offen. 2,918,878 (Nov. 22, 1979).
Haken, P. T. et al., Chemical Abstract 93:132471; (1980), Abstracting Brit. Pat. Appln. 2,024,218 (Jan. 9, 1980).

*Primary Examiner*—Donald G. Daus
*Assistant Examiner*—Barbara Cassatt

[57] ABSTRACT

Substituted 3,5-diphenyl-3-(1H-imidazol-1-ylmethyl)-2-methylisoxazolidines in which hydrogens of their phenyl rings may be replaced by halogen, lower alkoxy or lower alkyl groups are useful as antifungal agents.

11 Claims, No Drawings

SUBSTITUTED 3,5-DIPHENYL-3-(1H-IMIDAZOL-1-YLMETHYL)-2-METHYLISOXAZOLIDINES

BACKGROUND OF THE INVENTION

This invention relates generally to substituted 2-methylisoxazolidine derivatives and more specifically to substituted 3,5-diphenyl-3-(1H-imidazol-1-ylmethyl)-2-methylisoxazolidines which are useful as antifungal agents.

BRIEF SUMMARY OF THE INVENTION

In accordance with this invention there are provided compounds of the formula:

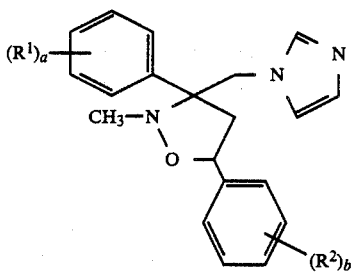

and the pharmaceutically acceptable acid addition salts, thereof, in the form of their enantiomers, or mixtures of their enantiomers including diastereoisomeric pairs of such enantiomers, wherein:
- a=1 or 2,
- b=1 or 2,
- $R^1$ is selected from hydrogen, halogen, lower alkyl, lower alkoxy, and combinations thereof, provided that the ortho position is hydrogen, and
- $R^2$, selected from hydrogen, halogen, lower alkyl, lower alkoxy, and combinations thereof.

DETAILED DESCRIPTION OF THE INVENTION

The compounds of this invention are useful antifungal agents. They have been shown to possess activity against yeast and systemic mycoses and dermatophytes as determined by broth and agar testing techniques [McGinnes, M.R., *Laboratory Handbook of Medical Mycology*, Academic Press, N.Y., N.Y. (1980]. The compounds prepared in Examples 1 to 7 below were tested and found to have good inhibitory activity against a broad spectrum of organisms including trichophyton mentagrophytes, trichophyton tonsurans, trichophyton rubrum, trichophyton schoenleinii, epidermophyton floccosum, microsporum canis, and candida stellatoidea (minimum inhibitory concentration, MIC, of <0.2 to 20 ug/ml).

Because of the antifungal activity of the compounds of the invention they can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal injections in warm blooded animals (1 to 20 percent active ingredient).

The compounds of this invention are those of the formula:

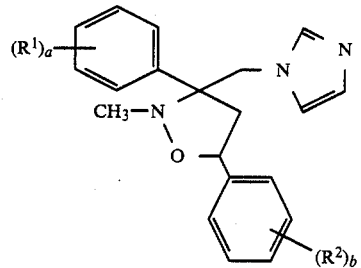

and the pharmaceutically acceptable acid addition salts thereof, in the form of their enantiomers or mixtures of their enantiomers including diastereoisomeric pairs of such enantiomers, wherein;
- a=1 or 2,
- b=1 or 2,
- $R^1$ is selected from hydrogen, halogen, lower alkyl, lower alkoxy, and combinations thereof, provided that the ortho position is hydrogen, and
- $R^2$ is selected from hydrogen, halogen, lower alkyl, lower alkoxy and combinations thereof.

By lower alkyl and lower alkoxy is meant $C_1$ to $C_4$ which can be a branched or unbranched chain. Compounds having ortho substitution of the upper phenyl group were not prepared probably due to steric hindrance. By halogen is meant chlorine, bromine, fluorine and iodine with chlorine and fluorine being preferred.

The substituted 3,5-diphenyl-3-(1H-imidazol-1-ylmethyl)-2-methyl-isoxazolidines are obtained as mixtures of cis- and trans-diastereomers due to the presence of two asymmetric carbon atoms in the isoxazolidine ring. The diastereomeric mixture is conveniently separated by flash-chromatography on silica gel using halogenated hydrocarbons (preferably dichloromethane and chloroform), alkanols (preferably methanol and ethanol), ethyl acetate and such, as eluents. The said eluents may be used alone or in combinations such as the ones comprised of 95–99% halogenated hydrocarbon and 1–5% alkanol by volume. The stereochemistry of the two asymmetric carbon atoms in the isoxazolidine ring may be determined by conventional methods that include x-ray crystallography, nuclear magnetic resonance spectroscopy, circular dichroism and optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−) tartaric acid, (+) and (−) dibenzoyltarataric acid and the like.

As illustrated in the following diagram, the compounds can be prepared starting with the reaction of a properly substituted 2-(1H-imidazol-1-yl) acetophenone (1) with N-methylhydroxylamine to give the corresponding nitrone derivative 2 as disclosed in our co-pending application filed concurrently herewith and commonly assigned entitled "β-substituted Ketonitrone Derivatives" whose disclosure is incorporated herein by reference. Treatment of compound 2 with an appropriate styrene derivative (3) provides a diastereomeric mixture of the desired cis- and trans-3,5-diphenyl-3-(1H-imidazol-1-ylmethyl)-2-methylisoxazolidine compound 4.

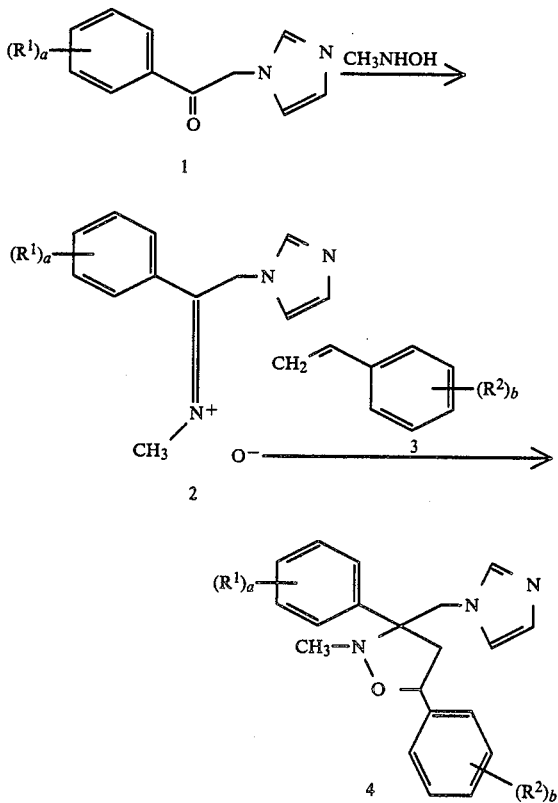

The compounds of the invention are basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following synthesis of intermediates and in the Examples.

PREPARATION OF IMIDAZOLYLACETOPHENONES (1)

The imidazolylacetophenone derivatives may be prepared according to the known procedures of (a) Godefroi et al., J. Medicinal Chem. 12, 784 (1969), and (b) Nardi et al., J. Medicinal Chem. 24, 727 (1981). The following imidazolylacetophenones (1) were synthesized:

(a) 2-(1H-imidazol-1-yl) acetophenone 117°–119° C., (b) 2-(1H-imidazol-1-yl)-4'-chloroacetophenone, mp. 152°–156° C., (c) 2-(1H-imidazol-1-yl)-4'-fluoroacetophenone, mp. 150°–155°, and (d) 2-(1H-imidazol-1-yl)-4'-methoxyacetophenone, mp. 111°–113° C.

Preparation of Styrene Compounds (3)

The styrene derivatives 3 are either commercially available, or may be prepared by standard procedures such as Wittig reaction of an appropriately substituted benzaldehyde with methylenetriphenylphosphorane [Wittig and Schoellkopf, Chem. Ber. 87, 1318 (1954)]. All styrene derivatives 3 used in the synthesis of the 3,5-diphenyl-3-(1H-imidazol-1-ylmethyl)-2-methylisoxazolidines (4) in the Examples are commercially available.

EXAMPLE 1

3,5-Bis(4-methoxyphenyl)-3-(1H-imidazol-1-ylmethyl)-2-methylisoxazolidine (4, $R^1 = R^2 = 4$—$OCH_3$)

Under a nitrogen atmosphere, a suspension of 21.75 g (0.101 mol) of 2-(1H-imidazol-1-yl)-4'-methoxyacetophenone (1, $R^1 = 4$—$OCH_3$), 11.89 g (0.142 mol) of N-methylhydroxylamine hydrochloride and 12.03 g (0.143 mol) of sodium bicarbonate in 250 ml of absolute ethanol was heated to reflux and stirred for 45 hours. After cooling to room temperature, the suspension was filtered and the solvent removed in vacuo. The residual orange oil, containing nitrone 2 ($R^1 = 4$—$OCH_3$) was taken up in chloroform, filtered and the solvent removed in vacuo. The oil was then dissolved in 250 ml of toluene, under a nitrogen atmosphere, and 25.0 g (0.186 mol) of 4-methoxystyrene (3, $R^2 = 4$—$OCH_3$) was added. The resulting solution was refluxed for 23 hours, cooled to room temperature, and the solvent removed in vacuo. The crude cis- and trans-diastereomeric mixture of compound 4 ($R^1 = R^2 = 4$—$OCH_3$) was purified by flash-chromatography on neutral silica gel using ethyl acetate as eluent.

Isomer A had a melting point of 117°–120° C. (ethyl acetate).

Anal. Calcd. for $C_{22}H_{25}N_3O_3$: C, 69.64; H, 6.64; N, 11.07. Found: C, 69.57; H, 6.85; N, 10.88.

EXAMPLE 2

3,5-Diphenyl-3-(1H-imidazol-1-ylmethyl)-2-methylisoxazolidine (4, $R^1 = R^2 = H$)

Compound 4 ($R^1 = R^2 = H$) was prepared by a procedure similar to that described in Example 1, by reacting 2-(1H-imidazol-1-yl)acetophenone (1, $R^1 = H$) with N-methylhydroxylamine hydrochloride to form the corresponding nitrone derivative 2 ($R^1 = H$), and treating the latter with styrene (3, $R^2 = H$). The resulting cis- and trans-diastereomeric mixture of compound 4 ($R^1 = R^2 = H$) was purified by flash-chromatography on neutral silica gel using ethyl acetate as eluent.

Isomer A had a melting point of 97°–99° C. (ethyl ether).

Anal.

Calcd. for $C_{20}H_{21}N_3O$: C, 75.21; H, 6.63; N, 13.16. Found: C, 75.14; H, 6.71; N, 13.14.

Isomer B had a melting point of 200°–202° C. (methanol).

Anal. Calcd. for $C_{20}H_{21}N_3O$: C, 75.21; H, 6.63; N, 13.16. Found: C, 75.07; H, 6.73; N, 13.12.

EXAMPLE 3

3-(4-Chlorophenyl)-3-(1H-imidazol-1-ylmethyl)-2-methyl-5-phenylisoxazolidine (4, $R^1 = 4$—Cl, $R^2 = H$)

Compound 4 ($R^1 = 4$—Cl, $R^2 = H$) was prepared by a procedure similar to that described in Example 1, by reacting 2-(1H-imidazol-1-yl)-4'-chloroacetophenone (1, $R^1 = 4$—Cl) with N-methylhydroxylamine hydrochloride to form the corresponding nitrone derivative 2 ($R^1 = 4$—Cl), and treating the latter with styrene (3, $R^2 = H$). The resulting cis- and trans-diastereomeric mixture of compound 4 ($R^1 = 4$—Cl, $R^2 = H$) was purified by flash-chromatography on neutral silica gel using a 98:2 by volume mixture of chloroform and methanol as eluent.

Isomer A had a melting point of 159°–163° C. (ethyl acetate).

Anal. Calcd. for $C_{20}H_{20}ClN_3O$: C, 67.89; H, 5.70; N, 11.88; Cl, 10.02, found: C, 67.78; H, 5.80; N, 11.83; Cl, 9.94.

Isomer B had a melting point of 124°–127° C. (ethyl acetate-hexane, 1:1 by volume).

EXAMPLE 4

3,5-Bis(4-chlorophenyl)-3-(1H-imidazol-1-ylmethyl)-2-methylisoxazolidine (4, $R^1=R^2=4$—Cl)

Compound 4 ($R^1=R^2=4$—Cl) was prepared by a procedure similar to that described in Example 1, by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and reacting the latter with 4-chlorostyrene (3, $R^2=4$—Cl). The resulting cis- and trans-diastereomeric mixture of compound 4 ($R^1=R^2=4$—Cl) was purified by extraction of the toluene solution with 2 N hydrochloric acid, neutralization of the aqueous acid layer with solid potassium carbonate, and back-extraction with chloroform.

Isomer A had melting point of 137°–139° C. (ethyl acetate).

Anal. Calcd. for $C_{20}H_{19}Cl_2N_2O$: C, 61.87; H, 4.93; N, 10.82. Found: C, 61.73; H, 4.99; N, 10.81.

The preparation of the title compound 4 ($R^1=R^2=4$—Cl) was repeated except that the nitrone 2 was prepared using sodium acetate rather than sodium bicarbonate.

EXAMPLE 5

5-(2-Chlorophenyl)-3-(4-chlorophenyl)-3-(1H-imidazol-1-yl-methyl)-2-methylisoxazolidine (4, $R^1=4$—Cl, $R^2=2$—Cl)

Compound 4 ($R^1=4$—Cl, $R^2=2$—Cl) was prepared by a procedure similar to that described in Example 1, by reacting 2-(1H-imidazol-1-y)-4-'chloroacetophenone (1, $R^1=4$—Cl) with N-methylhydroxylamine hydrochloride to form the corresponding nitrone derivative 2 ($R^1=4$—Cl), and treating the latter with 2-chlorostyrene (3, $R^2=2$—Cl). The resulting cis- and trans-diastereomeric mixture of compound 4 ($R^1=4$—Cl, $R^2=2$—Cl) was purified by flash-chromatography on neutral silica gel using a 95:5 by volume mixture of chloroform and methanol as eluent.

Isomer A had a melting point of 129°–132° C. (ethyl acetate).

Anal. Calcd. for $C_{20}H_{19}Cl_2N_3O$: C, 61.87; H, 4.93; N, 10.82. Found: C, 61.77; H, 5.00: N, 10.77.

EXAMPLE 6

3-(4-Chlorophenyl)-5-(2,6-dichlorophenyl)-3-(1H-imidazol-1-yimethyl)-2-methylisoxazolidine (4, $R^1=4$—Cl, $R^2=2,6$—Cl$_2$)

Compound 4 ($R^1=4$—Cl, $R^2=2,6$—Cl$_2$) was prepared by a procedure similar to that described in Example 1, by reacting 2-(1H-imidazol-1-yl)-4'-chloroacetophenone (1, $R^1=4$—Cl) with N-methylhydroxylamine hydrochloride to form the corresponding nitrone derivative 2 ($R^1=4$—Cl), and treating the latter with 2,6-dichlorostyrene (3, $R^2=2,6$—Cl$_2$). The resulting cis- and trans- diastereomeric mixture of compound 4 ($R^1=4$—Cl, $R^2=2,6$—Cl$_2$) was purified by flash-chromatography on neutral silica gel using ethyl acetate as eluent.

Isomer A had a melting point of 159°–161° C. (ethyl acetate).

Anal. Calcd. for $C_{20}H_{18}Cl_3N_3O$: C, 56.82; H, 4.29; N, 9.94. Found: C, 56.90; H, 4.50; N, 9.73

Isomer B, had a melting point of 64°–66° C. (isopropanol) as its 1:1 complex with isopropanol.

Anal, Calcd. for $C_{20}H_{18}Cl_3N_3O \cdot C_3H_8O$: C, 57.21; H, 5.43; N, 8.70; Cl, 22.03 Found: C, 57.20; H, 5.40; N, 8.74; Cl, 22.12.

EXAMPLE 7

3-(4-Chlorophenyl)-3-(1H-imidazol-1-ylmethyl)-2-methyl-5-(4-methylphenyl)isoxazolidine (4, $R^1=4$—Cl, $R^2=4$—CH$_3$)

Compound 4 ($R^1=4$—Cl, $R^2=4$—CH$_3$) was prepared by a procedure similar to that described in Example 1, by reacting (1H-imidazol-1-yl)-4'-chloroacetophenone (1, $R^1=4$—Cl) with N-methylhydroxyamine hydrochloride to form the corresponding nitrone derivative 2 ($R^1=4$—Cl), and treating the latter with 4-methylstyrene (3, $R^2=4$—CH$_3$). The resulting cis- and trans-diastereomeric mixture of compound 4, ($R^1=4$—Cl, $R^2=4$—CH$_3$) was purified by flash-chromatography on neutral silica gel using a 98:2 by volume mixture of chloroform and methanol as eluent.

Isomer A had a melting point of 135.5°–137° C. (ethyl acetate).

Anal. Calcd. for $C_{21}H_{22}ClN_3O$: C, 68.56; H, 6.03; N, 11.42; Cl, 9.64. Found: C, 68.40; H, 6.10; N, 11.26; Cl, 9.67.

Isomer B had a melting point of 129° C. (ethyl acetate).

Anal. Calcd. for $C_{21}H_{22}ClN_3O$: C, 68.56; H, 6.03; N, 11.42; Cl, 9.64. Found: C, 68.67; H, 6.14; N, 11.44; Cl, 10.06

EXAMPLE 8

3-(4-Fluorophenyl)-3-(1H-imidazol-1-ylmethyl)-2-methyl-5-phenylisoxazolidine (4, $R^1=4$—F, $R^2=H$)

Compound 4 ($R^1=4$—F, $R^2=H$) was prepared by a procedure similar to that described in Example 1, by reacting 2-(1H-imidazol-1-yl)-4'-fluoroacetophenone (1, $R^1=4$—F) with N-methylhydroxylamine hydrochloride to form the corresponding nitrone derivative 2 ($R^1=4$—F), and treating the latter with styrene (3, $R^2=H$). The resulting cis- and trans-diastereomeric mixture of compound 4 ($R^1=4$—F, $R^2=H$) was purified by flash-chromatography on neutral silica gel using a 98:2 by volume mixture of chloroform and methanol as eluent.

Isomer A had a melting point of 130°–132° C. (ethyl acetate).

Anal. Calcd. for $C_{20}H_{20}FN_3O$: C, 71.20; H, 5.97; N, 12.45; F, 5.63. Found: C, 71.33; H, 6.52; N, 12.46; F, 5.64.

EXAMPLE 9

5-(3,4-Dimethoxyphenyl)-3-(1H-imidazol-1-ylmethyl)-2-methyl-3-phenylisoxazolidine (4, $R^1=H$, $R^2=3,4$—(OCH$_3$)$_2$]

Compound 4 [$R^1=H$, $R^2=3,4$—(OCH$_3$)$_2$] was prepared by a procedure similar to that described in Example 1, by reacting 2-(1H-imidazol-1-yl)acetophenone (1, $R^1=H$) with N-methylhydroxylamine hydrochloride to form the corresponding nitrone derivative 2 ($R^1$=H), and treating the latter with 3,4-dimethoxystyrene [3, $R^2$=3,4—(OCH$_3$)$_2$]. The resulting cis- and trans-diastereomeric mixture of compound 4 [$R^1$=H, $R^2$=3,4—(OCH$_3$)$_2$] was purified by flash-chromatography on neutral silica gel using a 98:2 by volume mixture of chloroform and methanol as eluent.

Isomer A had a melting point of 136°–144° C. (isopropanol) as its monohydrochloride salt which was prepared by dissolving the compound in an ethanol-concentrated HCl mixture (10:1 by volume), evaporating the solvent and then recrystallizing the acid salt from methanol-ether, 1:3 by volume.

Salts with other acids and salts of other compounds of the invention can be prepared in a similar manner.

We claim:

1. A compound of the formula:

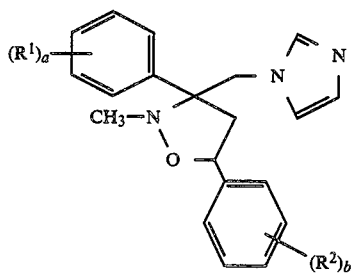

or a pharmaceutically acceptable acid addition salt thereof, in the form of their enantiomers or mixtures of their enantiomers including diastereoisomeric pairs of such enantiomers, wherein;

a=1 or 2,
b=1 or 2,
$R^1$ is selected from hydrogen, halogen, lower alkyl, lower alkoxy, and combinations thereof, provided that the ortho position is hydrogen, and
$R^2$ is selected from hydrogen, halogen, lower alkyl, lower alkoxy, and combinations thereof.

2. The compound of claim 1 wherein the compound is 3,5-bis(4-methoxyphenyl)-3-(1H-imidazol-1-ylmethyl)-2-methylisoxazolidine.

3. The compound of claim 1 wherein the compound is 3,5-diphenyl-3-(1y-imidazol-1-ylmethyl)-2-methylisoxazolidine.

4. The compound of claim 1 wherein the compound is 3-(4-chlorophenyl)-3-(1H-imidazol-1-ylmethyl)-2-methyl-5-phenylisoxazolidine.

5. The compound of claim 1 wherein the compound is 3,5-bis(4-chlorophenyl)-3-(1H-imidazol-1-ylmethyl)-2-methylisoxazolidine.

6. The compound of claim 1 wherein the compound is 5-(2-chlorophenyl)-3-(4-chlorophenyl)-3-(1H-imidazol-1-yl-methyl)-2-methylisoxazolidine.

7. The compound of claim 1 wherein the compound is 3-(4-chlorophenyl)-5-(2,6-dichlorophenyl)-3-(1H-imidazol-1-ylmethyl)-2-methylisoxazolidine.

8. The compound of claim 1 wherein the compound is 3-(4-chlorophenyl)-3-(1H-imidazol-1-methyl)-2-methyl-5-(4-methylphenyl)isoxazolidine.

9. The compound of claim 1 wherein the compound is 3-(4-fluorophenyl)-3-(1H-imidazol-1-ylmethyl)-2-methyl-5-phenylisoxazolidine.

10. The compound of claim 1 wherein the compound is 5-(3,4-dimethoxyphenyl)-3-(1H-imidazol-1-ylmethyl)-2-methyl-3-phenylisoxazolidine.

11. The compound of claim 1 wherein the compound is a diastereoisomeric pair of enantiomer.

* * * * *